United States Patent [19]

Mao et al.

[11] 4,092,412

[45] May 30, 1978

[54] TREATMENT OF HERPES SIMPLEX INFECTIONS

[75] Inventors: James Chieh-Hsia Mao, Libertyville; John Hunter Seely, Lake Forest; John Scott Fairgrieve, Lake Villa, all of Ill.

[73] Assignee: Abbott Laboratories, North Chicago, Ill.

[21] Appl. No.: 787,687

[22] Filed: Apr. 14, 1977

Related U.S. Application Data

[63] Continuation-in-part of Ser. No. 681,875, April 30, 1976, abandoned.

[51] Int. Cl.$^2$ ............................................. A61K 31/66
[52] U.S. Cl. .................................................... 424/212
[58] Field of Search ........................................ 424/212

[56] References Cited

PUBLICATIONS

Chemical Abstracts 60:4180f (1964).

*Primary Examiner*—Jerome D. Goldberg
*Attorney, Agent, or Firm*—Paul D. Burgauer; Robert L. Niblack

[57] ABSTRACT

A method of treating herpes simplex infections in warm-blooded animals by administering to said animals a carboxylic ester of phosphonoacetic acid of the formula

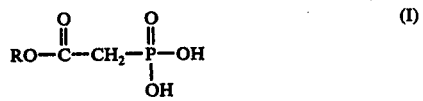

(I)

wherein R is a $C_1$–$C_2$ alkyl.

6 Claims, No Drawings

TREATMENT OF HERPES SIMPLEX INFECTIONS

BACKGROUND OF THE APPLICATION

This application is a continuation-in-part of our earlier filed U.S. patent application, Ser. No. 681,875, filed on Apr. 30, 1976 now abandoned.

BACKGROUND OF THE INVENTION

Herpes virus infections, though known, are difficult to treat because of the lack of effective drugs. An effective anti-herpes drug could be used in the treatment or prevention of herpes dermatitis, herpes genitalis, herpes keratitis, herpes encephalitis and as provided by the present invention, herpes simplex virus. Although herpes simplex is a very common, though minor disease, the only basic treatment presently available is the application of idoxuridine.

DETAILED DESCRIPTION OF THE INVENTION

This invention relates to a method of treating the effect of herpes simplex infections in warm-blooded animals comprising administering to such infected animal, a compound containing a carboxylic ester of phosphonoacetic acid of the structure

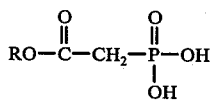

(I)

wherein R is a $C_1$–$C_2$ alkyl, or a pharmaceutically acceptable salt thereof. In a preferred embodiment, the above composition is an ointment, lotion, solution, or emulsion for topical application and contains between 0.2 and 10.0% by weight of compound I.

The ester compounds are active against herpes simplex virus in tissue culture. They are also active in vivo when administered either as the acid or the alkali metal salts, particularly the mono and di sodium, and calcium salts. The compounds are preferably administered topically, but can also be given by the oral or intraperitoneally (i.p.) route.

Since the herpes viruses depend for replication upon a unique DNA polymerase independent from the DNA polymerase of the mammalian host, growth of the virus may be stopped by inhibiting this necessary enzyme. These carboxyl esters of phosphonoacetic acid are potent inhibitors of the enzyme.

The present carboxylic esters of phosphonoacetic acid can be prepared according to the procedure described in the publication of G. M. Kosolapoff, "Organophosphorus", John Wiley, N.Y. (1950), p. 160. The carboxylic esters that may be prepared according to the method of G. M. Kosolapoff include:

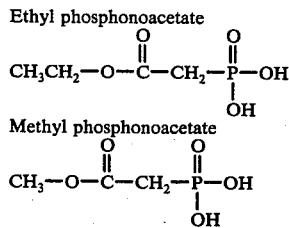

Compounds II and III are viscous nonvolatile oils and therefore do not possess melting or boiling points. In order to identify the compounds, Table I below lists the characteristic Nuclear Magnetic Resonance (NMR) signals of each of the above compounds.

TABLE I
CHARACTERISTIC NMR SIGNAL OF CARBOXYLIC ESTERS OF PHOSPHONOACETIC ACID

| Compound | Solvent | Chemical Shift of Methylene-Phosphorus (ppm from TMS) | Chemical Shift of Additional Signals (ppm from TMS) |
|---|---|---|---|
| II | $CDCl_3$ | 3.11d | 4.26 (—O—$CH_2$—$CH_3$)q<br>1.26 (O$CH_2CH_3$)t |
| III | TFA | 3.4d | 3.9 (—$CH_3$)s |

$CDCl_3$ = deuterochloroform,
TFA = Trifluoroacetic acid
d = doublet, q = quartet, t = triplet, s = singlet

EXAMPLE 1

Herpes Simplex Viruses

Isolation and Purification of Herpes Simplex Type 2 Deoxyribonucleic Acid (DNA) Polymerase Herpes virus infected Wi-38 cells were grown and harvested when 25% of the cells showed cytopathic effect of the virus. The DNA polymerase was isolated according to the procedure of Smith and Gallo (1972) which involved column chromatography on DEAE-cellulose and phosphocellulose. However, buffer containing 20% glyceryl instead of 10% was used. The final enzyme preparation has a specific activity of 313 unit/mg. for herpes simplex virus type 2.

Viral Deoxyribonucleic Acid (DNA) Polymerase Assay

The reaction mixture (0.2 ml.) contains 10 $\mu$M of 2'-deoxyadenosine-5'-triphosphate, 2'-deoxycytidine-5'-triphosphate, 2'-deoxyguanosine-5'-triphosphate, and 2.5 $\mu$M tritium labeled thymidine-5'-triphosphate which was appropriately diluted with unlabeled dTTP to give 880 counts per minute per pico-mole, 10 $\mu$g of activated calf thymus DNA 50 mM Tris-HCl buffer (pH 8.0), 3mM $MgCl_2$, 100 mM KCl and 1 mM dithiothritol. The amounts of enzyme used in each reaction was chosen to give a linear rate for at least 30 minutes at 37° C. The reaction was terminated by the addition of 3 ml. of cold 5% trichloroacetic acid - 0.01 M sodium pyrophosphate. The acid-insoluble material was collected, washed twice on glass filter discs (Reeve Angel 984-H) and the incorporated $^3$H-dTMP was determined by a liquid scintillation counter.

The effect of each of the compounds in the inhibition of Herpes simplex type 2 deoxyribonucleic acid (DNA) is recorded below in Table II

TABLE II
INHIBITION OF HERPES SIMPLEX TYPE 2

| Compound | Concentration ($\mu$g/ml) | Percent Inhibition |
|---|---|---|
| II | 3.9 | 50% |
| III | 7.0 | 50% |

EXAMPLE 2

Determination of Antiviral Activity by Plaque Reduction Method

The inhibitory effect of new compounds upon herpes simplex virus (HSV) type 1 or type 2 was analyzed by the plaque reduction assay. Confluent monolayers of rabbit kidney cells grown in 60 mm plastic petri dishes were infected with HSV by adsorption for 1 hour at room temperature. The appropriate concentration of the test compound was added at the time of initial virus infection. Following virus adsorption the cells were overlayed with Eagle's medium (BME) supplemented with 10% fetal bovine serum, 0.225% $NaHCO_3$ and 0.5% methycellulose. The appropriate concentration of the test compound was also added to this overlay. Infected cultures were then incubated at 37° C. for the remainder of the test. Three to four days following virus infection, each culture was stained with crystal violet and the herpes virus induced plaques counted. Inhibition of virus replication was determined by comparing the number of herpes virus plaques in the presence of the test compound to the number of herpes virus plaques in the absence of the test compound, as indicated in Table III, below:

TABLE III

| INHIBITION OF PLAQUES BY COMPOUNDS | |
|---|---|
| Compound | Inhibition |
| Infected Cells (Control) | 0 |
| Compound II | +4 |
| Compound III | +2 |

0 = inactive, +2 = moderate activity, +4 = very active.

EXAMPLE 3

Ethyl Phosphonoacetate

Into 100 ml. of absolute ethanol was placed 28 g. (0.2 mole) of phosphonoacetic acid. The solution was treated with a stream of dry hydrogen chloride at 0° C. for 45 minutes. After refluxing for 3 hours the solution was allowed to stand overnight at room temperature. Evaporation of the solvent yielded a viscous oil, which was dried in vacuo over $P_2O_5$ and NaOH.

EXAMPLE 4

Methyl Phosphonoacetate

Phosphonoacetic acid, 5 g., was dissolved in 25 ml. methyl alcohol. Dry hydrogen chloride was bubbled through the solution for 30 minutes at 0° C. The solution was refluxed for 4 hours. Evaporation of the solvent left an oil which was dried in vacuo over $P_2O_5$ and NaOH.

EXAMPLE 5

Topical Test

The following test was applied to determine the effectiveness of the carboxylic esters of phosphonoacetic acid against herpes simplex infections in mice. The compounds tested included the compounds shown above as II and III. Also included were a standard virus control as well as a normal (no virus) control.

In the tests, 20 gram female CF mice, under light ether anesthesia, had a 20-mm square area of their backs plucked free of hair. Herpes virus ($10^7$ $TCID_{50}$/ml) was applied topically (0.05 ml) to the denuded skin and impregnated into the dermis with a 24-gauge sterile hypodermic needle. In untreated animals, herpes lesions or vesicles usually develop in 3 to 5 days. The lesions form bands which extend over the denuded area. After approximately 10 days, mice usually develop a paralysis which results in their death. The test was allowed to continue for a total of 14 days.

Some of the animals were treated topically by having the drug applied to the site of infection as a 2% aqueous solution 2 hours after the virus was introduced into the skin, and twice daily for 5 consecutive days. The drug was applied a total of 11 times. A single application of a 2% drug solution delivered approximately 2 mg of material.

The Mann-Whitney "U" Test was used to statistically analyze the herpes infection in mice by making paired comparisons between the treated and untreated virus control groups. Those groups that showed statistically significant differences (P <0.10) from the virus control group were defined "active". The result of the test is recorded in the following table:

| | EFFECT AGAINST HERPES SIMPLEX INFECTIONS IN CF MICE | | | | |
|---|---|---|---|---|---|
| Treatment | No. of Mice | Route (Topical) | No. of Mice Dead | No. of Mice Paralyzed | Significant Level |
| Normal Control | 10 | — | 0 | 0 | |
| Virus Control | 10 | — | 7 | 3 | |
| Compound II | 10 | 2% | 3 | 2 | P <.05 |
| Compund III | 10 | 2% | 5 | 2 | P <.10 |

In the above examples, the compounds of this invention were used topically as a 2% aqueous solution which can easily be replaced by a similar solution, emulsion or lotion using other liquid, suspendable or soluble diluents. For instance, a solution containing 0.2 to 10% by weight of the compound of formula II or III, or their pharmaceutically acceptable salts, in 70% aqueous ethanol can be used, and the usual preservatives, coloring components and the like may be added.

The above compounds or their pharmaceutically acceptable salts can also be topically applied as an ointment. A standard ointment uses the above compound at a weight concentration of 0.2 to 10% by weight, homogeneously blended into Pramme cream or petrolatum.

For applications other than topical, the above compounds may be absorbed on an inert carrier and placed in capsules or compressed into tablets for oral administration. For parenteral administration, aqueous solutions containing the usual preservatives and containing between 0.2 and 20% by weight of the above compound are easily prepared and can be used in such form.

We claim:

1. A method for treating herpes simplex virus infection in a warm-blooded animal which comprises administering to an animal so infected, an effective amount to combat said virus of a composition containing a carboxylic ester of phosphonoacetic acid of the formula

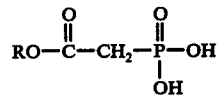

wherein R is a $C_1$-$C_2$ alkyl or a pharmaceutically acceptable salt thereof.

2. A method according to claim 1 wherein said carboxylic ester is ethyl phosphonoacetate.

3. A method according to claim 1 wherein said carboxylic ester is methyl phosphonoacetate.

4. A method for treating herpes simplex virus infection in a warm-blooded animal which comprises topically administering to an animal so infected an effective amount of a composition containing, as the active ingredient, methyl or ethyl phosphonoacetate or a topically acceptable salt thereof in a pharmaceutically acceptable carrier of diluent, said active ingredient being present in an amount of between 0.2 and 20% by weight.

5. The method of claim 4 wherein said carrier is an ointment base.

6. The method of claim 4 wherein said carrier is water.